US008568345B2

(12) United States Patent
Ryscavage

(10) Patent No.: US 8,568,345 B2
(45) Date of Patent: Oct. 29, 2013

(54) DIGIT PAD FOR TREATING TRIGGER FINGER AND TRIGGER THUMB

(76) Inventor: Thomas S. Ryscavage, York, PA (US)

( * ) Notice: Subject to any disclaimer, the term of this patent is extended or adjusted under 35 U.S.C. 154(b) by 1195 days.

(21) Appl. No.: 12/287,121

(22) Filed: Oct. 6, 2008

(65) Prior Publication Data

US 2009/0043233 A1    Feb. 12, 2009

Related U.S. Application Data

(63) Continuation of application No. 11/333,149, filed on Jan. 17, 2006, now Pat. No. 7,458,946.

(51) Int. Cl.
*A61F 5/00*          (2006.01)
(52) U.S. Cl.
USPC ............................................. 602/20; 602/22
(58) Field of Classification Search
USPC ......... 602/20–23; 2/16, 20, 21, 161; 128/878, 128/879, 880
See application file for complete search history.

(56) References Cited

U.S. PATENT DOCUMENTS

| 4,194,736 | A | * | 3/1980 | Loafman ......................... 473/61 |
| 5,363,508 | A | * | 11/1994 | Kim .................................... 2/21 |
| D373,225 | S | * | 8/1996 | Theroux et al. .............. D29/114 |
| 5,634,854 | A | * | 6/1997 | Albertsson .................... 473/213 |
| 6,647,549 | B2 | * | 11/2003 | McDevitt et al. .................. 2/21 |

* cited by examiner

*Primary Examiner* — Michael A. Brown
(74) *Attorney, Agent, or Firm* — Stuart J. Friedman

(57) ABSTRACT

A digit pad for treating trigger finger and trigger thumb includes a digit band which is slid over the affected digit to a position between the PIP and the MCP joints and a palm pad which extends from the proximal end of the digit band toward the wrist, the palm pad being dimensioned and positioned to overlie a portion of the palm to at least cover the A1 pulley, the proximal end of the palm pad extending beyond the A1 pulley, but not beyond the proximal palmer crease, the palm pad being at least as wide as the A1 pulley and being formed of a material which is soft, flexible, resilient and has a sufficient density to protect the palm area which it overlies.

9 Claims, 3 Drawing Sheets

DIGIT PAD FOR TREATING TRIGGER FINGER AND TRIGGER THUMB

CROSS REFERENCE TO RELATED APPLICATIONS

This application is a continuation of presently pending U.S. application Ser. No. 11/333,149, filed Jan. 17, 2006.

FIELD OF THE INVENTION

The present invention relates to a device and a method for treating trigger finger and trigger thumb and, more particularly, to a pad for mounting on a digit affected with trigger finger or trigger thumb which extends onto the palm a sufficient distance to at least cover the A1 pulley of the affected digit.

BACKGROUND OF THE INVENTION

Referring to FIG. 1, which shows the palm side of a human hand, it can be seen that the tendons pass into the digits inside a tendon sheath. This sheath functions to keep the synovial fluid around the tendon within the sheath. The synovial fluid lubricates the tendon as it moves back and forth in the digit. The beginning of the sheath, at the base of the digit, is called the A1 pulley. The purpose of the pullies is to keep the tendons close to the bone. As the digit bends, the pullies prevent the tendons from sagging away from the bone. The A1 pulley is the area that is involved in trigger finger or trigger thumb.

It is not known exactly what causes trigger finger or trigger thumb. However, it is generally believed that a contributing factor is impact on the palm of the hand. The tendon is subjected to significant forces at the A1 pulley, where trigger finger or thumb occurs. The tendon swells or forms a nodule at the base of the digit and has difficulty passing through the tendon sheath at the A1 pulley. The result is a painful "popping" or "snapping" of the digit in the palm at the location of the A1 pulley as the swollen part of the tendon passes the A1 pulley. As the condition worsens, the "popping" or "snapping" becomes more frequent. In serious cases, the swelling in the tendon cannot pass the A1 pulley and the digit is locked in position, i.e., it cannot bend or cannot be straightened.

Trigger finger or thumb does not seem to be related to any particular trauma event but, rather, comes on gradually. It typically affects people in their 40's, 50's and 60's and is about two to three times more common in women than in men. It can affect any digit or more than one digit on a hand at the same time or the digits of both hands at the same time. It is not uncommon for patients to be affected in more than one digit. The fourth digit is the digit most often involved.

Trigger finger or thumb is generally treated by splinting and/or steroid injections and/or surgery. Splinting has been found to be minimally effective and then only as long as the splint is worn. However, splints are very much disfavored by patients, are uncomfortable, limit the use of the digit and sometimes the hand and, generally, do not solve the problem of trigger finger or thumb. Multiple steroid injections in the affected digit have been found to be an effective treatment in many instances to resolve the problem of digit locking. However, the treatment is often only effective in the short term and, generally, does not completely resolve the problem of trigger finger or thumb. Approximately fifty percent of patients experiencing trigger finger or thumb go on to surgery. During the surgery, the tendon sheath is cut to allow the tendon to freely pass. The problem with surgery is that many patients recoil at the thought of it and will not have it done, preferring to live with the problem of trigger finger or thumb. Moreover, inherent in every surgery are the risks of anesthesia, infection, failure to relieve the triggering, recurrence of triggering and damage to other structures of the digit or hand.

Accordingly, there is a need for a non-surgical device and technique for the treatment of trigger finger and thumb which is effective in resolving the triggering, comfortable for the patient, easy to use and relatively inexpensive.

SUMMARY OF THE INVENTION

It is, therefore, a primary object of the present invention to provide a device which is useful for treating trigger finger or thumb comprising a digit band adapted to be slid over the affected digit and a palm pad unitary with the digit band, the palm pad being dimensioned and adapted to be positioned to overlie a portion of the palm to at least cover the A1 pulley of the affected digit.

It is another object of the present invention to provide a device which is useful for treating trigger finger or thumb wherein the palm pad is formed of a soft, flexible, resilient cushioning material which has sufficient density to be protective of the palm area which it overlies and to not deform when the affected hand is used, yet which is comfortable for a patient to wear substantially continuously during waking hours of the day for an extended period of weeks and which does not significantly interfere with the use or functioning of the affected digit or hand.

It is yet another object of the present invention to provide a device which is useful for treating trigger finger or thumb wherein the palm pad is dimensioned to at least cover the A1 pulley of the affected digit, desirably extends along the palm to the neck of the metacarpal bone of the affected digit but does not extend past the proximal palmar crease of the affected hand and preferably extends side-to-side a sufficient distance beyond the A1 pulley of the affected digit to substantially continuously cover the A1 pulley as the affected hand is used.

It is still another object of the present invention to provide a method for the treatment of trigger finger or thumb comprising placing upon each affected digit a device comprising a digit band surrounding the digit between its PIP and MCP joints and having a unitary palm pad which is positioned and dimensioned to overlie a portion of the palm to at least cover the A1 pulley of the affected digit.

The foregoing and other objects are achieved in accordance with the present invention by providing a device which is useful for treating trigger finger or thumb comprising a digit band adapted to be slid over the affected digit and a palm pad unitary with the digit pad, the palm pad being dimensioned and adapted to be positioned to overlie a portion of the palm to at least cover the A1 pulley of the affected digit.

In another aspect of the present invention, the palm pad is formed of a soft, flexible, resilient cushioning material which has sufficient density to be protective of the palm area which it overlies and to not deform when the affected hand is used, yet which is comfortable for a patient to wear substantially continuously during waking hours of the day for an extended period of weeks and which does not significantly interfere with the use or functioning of the affected digit or hand.

In still another aspect of the present invention, the palm pad extends from the digit band along the palm to the neck of the metacarpal bone of the affected digit but does not extend below the proximal palmar crease of the affected hand and extends side-to-side a sufficient distance beyond the A1 pulley of the affected digit to substantially continuously cover the A1 pulley as the affected hand is used.

In yet another aspect of the present invention, there is provided a method for the treatment of trigger finger or thumb comprising placing upon each affected digit a device comprising a digit band surrounding the digit between its PIP and MCP joints and having a unitary palm pad which is positioned and dimensioned to overlie a portion of the palm to at least cover the A1 pulley of the affected digit.

DESCRIPTION OF THE PREFERRED EMBODIMENT

Referring first to FIGS. 2-7, there is shown digit pad 10 of the present invention which is useful in the treatment of trigger finger and trigger thumb. Digit pad 10 includes a digit band 12 which is adapted to be slid onto and surround each digit which is affected with trigger finger or thumb. Therefore, multiple pads can be used on a hand if there are more than one trigger digits on the hand. Unitary with digit band 12 is palm pad 14 which is adapted to extend over and cover a portion of the palm of the hand. Preferably, digit band 12 is formed integrally with palm pad 14 by cutting an appropriate pattern from a single sheet of suitable material, as will be more fully described hereinafter, and the respective ends of the digit band 12 are attached in any suitable manner to form a seam 13 and an endless band. By way of illustration only, the respective ends of the digit band 12 may be advantageously attached by sewing, adhesive means or a combination of sewing and adhesive means. When sewing and/or adhesive attachment is employed, it is advantageous for the respective ends of the digit band 12 to attach over an area larger than the width of the digit band 12. To accomplish this, the respective ends of the digit band 12 may be slightly outwardly flared, as shown most clearly at 15 in FIG. 5, to cause the attachment seam to extend over a larger area. In an alternative form of the invention, digit band 12 and palm pad 14 may be separately formed and the band and pad attached by any suitable means.

Figure 1:
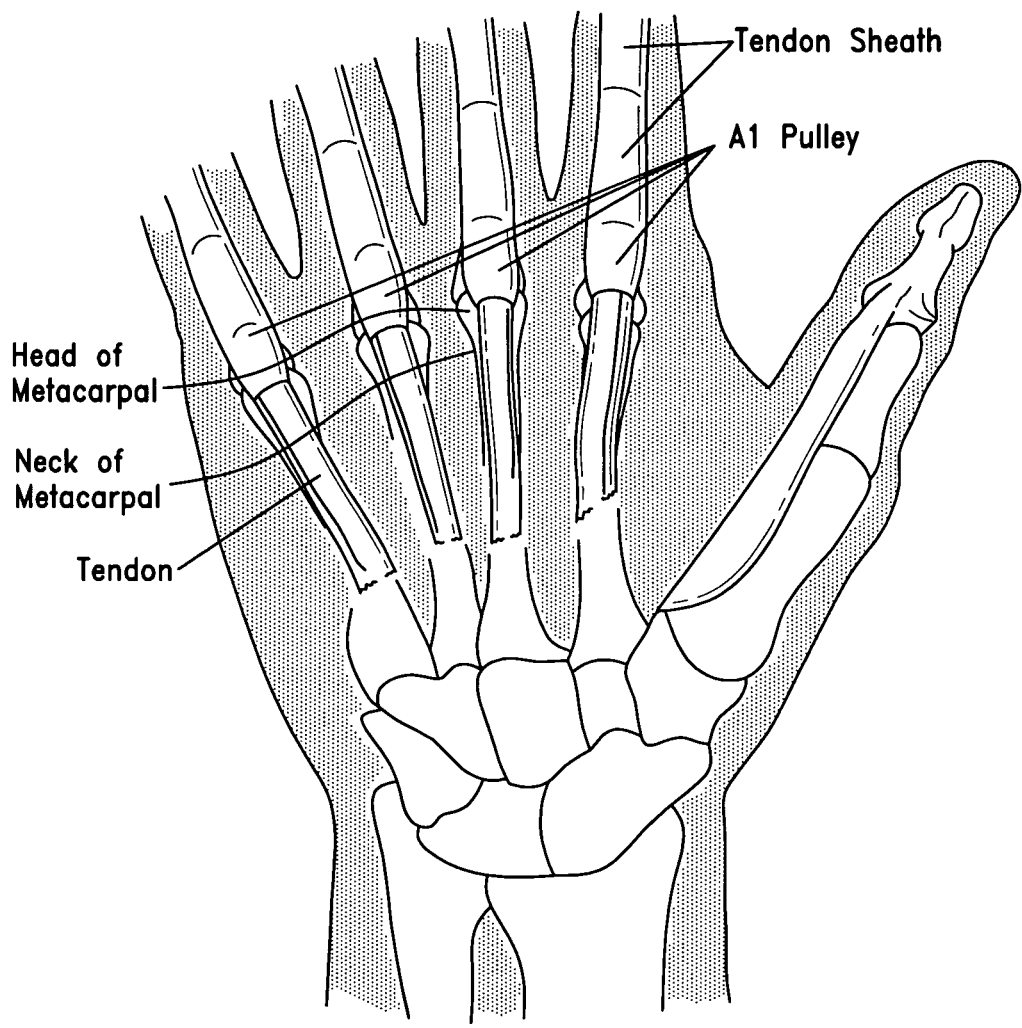
FIG. 1 is a plan view of the palm of a human hand showing the bones, tendons and tendon sheathing thereof.
Figure 2:
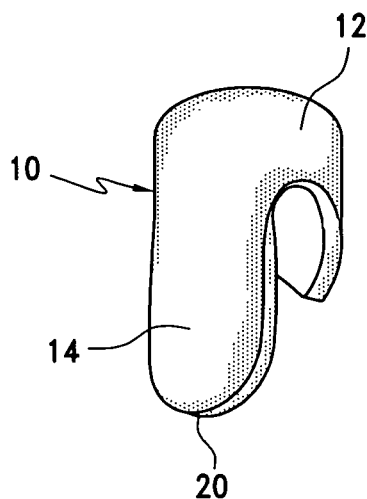
FIG. 2 is a perspective view of the digit pad of the present invention.
Figure 3:
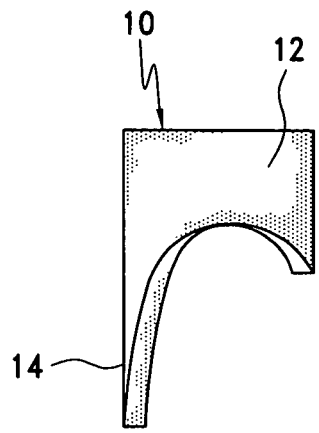
FIG. 3 is a right side elevational view of the digit pad of FIG. 2.
Figure 4:
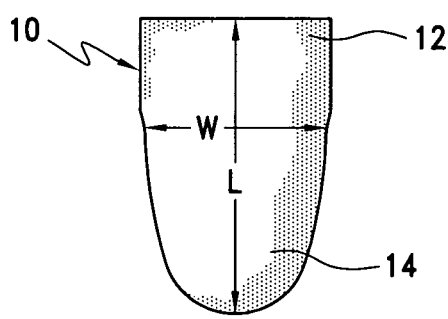
FIG. 4 is a front elevational view of the digit pad of FIG. 2.
Figure 5:
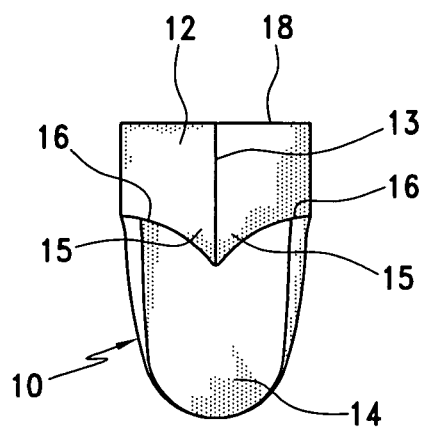
FIG. 5 is a rear elevational view of the digit pad of FIG. 2.
Figure 6:
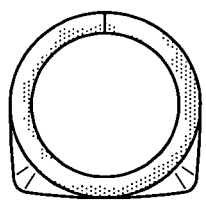
FIG. 6 is a top plan view of the digit pad of FIG. 2.
Figure 7:
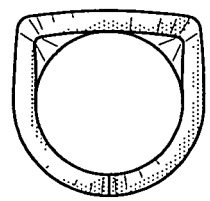
FIG. 7 is a bottom plan view of the digit pad of FIG. 2.
Figure 8:
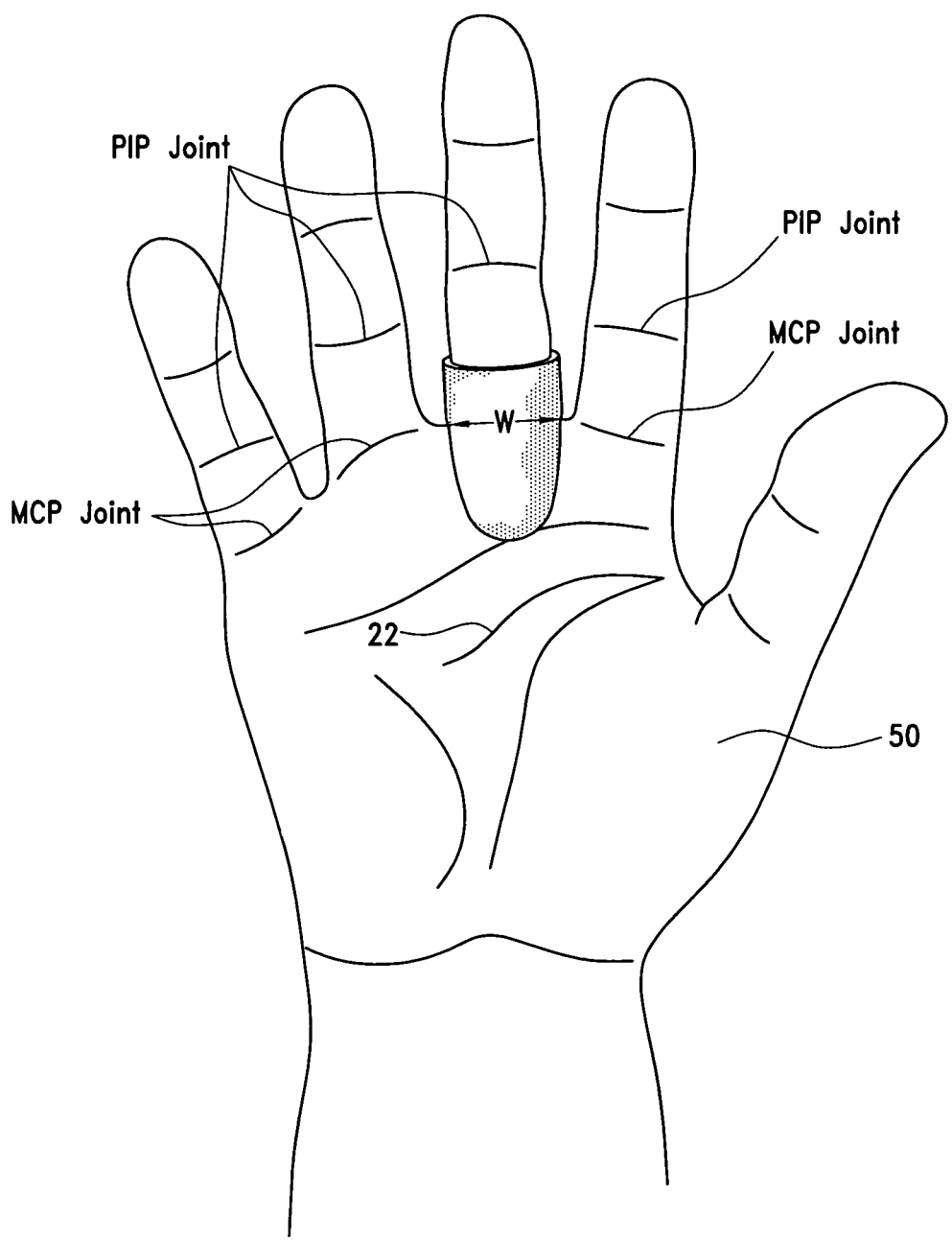
FIG. 8 is a perspective view of the palm of a human hand with the digit pad of FIG. 2 in position on the middle digit of the hand.

Referring to FIG. 8, the digit pad 10 is illustrated in place on a patient's hand 50. It is preferable for digit band 12 to encircle each affected digit between the proximal interphalangeal joint (PIP joint) and the metacarpo-phalangeal joint (MCP joint). The proximal end 16 of the digit band 12 is at the MCP joint, i.e., at the base of the digit and, desirably, the distal end 18 of the digit band 12 is located from one half to the full distance between the PIP and MCP joints. The palm pad 14 extends from the digit band 12 along the palm toward the wrist at least a sufficient distance to cover the A1 pulley and, desirably to a point on the palm more proximal than the A1 pulley. Desirably the proximal end 20 of the palm pad 14 extends a short distance beyond the A1 pulley to the neck of the metacarpal bone (see FIG. 1), but not beyond the proximal palmer crease 22 (see FIG. 8). Palm pad 14 is at least as wide as the A1 pulley in order to fully cover it. However, as a practical matter, as the patient uses the affected digit and hand, the palm pad 14 will move slightly. Therefore, it is preferred that the palm pad be somewhat wider (side to side dimension "W" as shown in FIGS. 4 and 8) than the A1 pulley, and that it extends a sufficient distance on each side of the A1 pulley of the affected digit to substantially continuously overlie the A1 pulley as the affected hand is used. Stated otherwise, the palm pad 14 should be wider than the A1 pulley but not so wide that it would interfere with similar pads on adjacent digits. A desirable width for the palm pad 14 is from 1.5 to 2 times the width of the A1 pulley. For comfort of the patient, the palm pad 14 may taper slightly from the digit band 12 toward its proximal end with its proximal end 20 defining a gentle curve.

Typically, the material from which the digit band 12 and the palm pad 14 are formed is the same, although this is not necessarily the case. The material of the digit band 12 may be any material which is comfortable for the patient to wear having in mind that it is located on a digit between the PIP and MCP joints, which is compatible with and easily attachable to the palm pad 14 and, desirably, which is somewhat elastic in order to better fit onto different diameter fingers. The palm pad 14 should be formed of a soft, flexible, cushioning material which has sufficient density to be protective of the palm area which it overlies and to not deform when the affected hand is used, yet which is comfortable for a patient to wear during substantially the entire day for an extended period of weeks and which does not significantly interfere with the use or functioning of the affected digit or hand. The material must not have a splinting or immobilizing effect. On the other hand, it should have excellent resistance to damage caused by flexing or bending as well as resistance to damage and deformation caused by water, oils and human perspiration. It should have a springy or resilient character in order to maintain its shape. It may not be hard, stiff or difficult to bend. Therefore, materials such as leather, plastic, metal, stone or wood should not be used.

One material found to be extremely desirable and advantageous for palm pad 14 is neoprene sheet laminated to very thin skin layers of nylon fabric on opposed faces of the sheet. Desirably, such a material may be used at a thickness of 3 mm to 5 mm, preferably 4 mm to 5 mm, depending on the density and compression set of the sheet. The nylon fabric contributes to patient comfort and maintains the cleanliness of the pad. One useful, commercially available material for forming the digit pad of the present invention is Rubatex® R-1400-N sheet with nylon fabric on opposed faces of the sheet, which is available from Rubatex Corporation of Bedford, Va. Rubatex® R-1400-N is a synthetic cellular rubber based on polychloroprene, has a density of about 8-15 lb/ft$^3$ and a 50% compression set of 35%. Other well known and substantially equivalent materials can also be used. Of particular usefulness are SBR neoprene sheets.

The digit pad of the present invention may be manufactured in a number of digit band diameters to accommodate the different hand sizes of patients. Generally, the length and width of the palm pad correspondingly increases and decreases with the digit band diameter. The digit pad may be manufactured with any combination of digit band diameters and overall digit pad lengths (i.e., the length "L" as shown in FIG. 4). By way of illustration only, a digit pad having a digit band diameter of from 1.25-1.5 cm might usefully have a digit pad length of 4.25-4.5 cm and a digit pad width "W", lying flat, just below the proximal end 18 of the digit band 12, of 2.5-2.75 cm.

In another embodiment of the present invention, there is provided a method for the treatment of trigger finger or thumb comprising placing upon each affected digit a digit pad 10, as hereinbefore described. The digit pad 10 is desirably worn by the patient on each affected digit substantially continuously during waking hours, desirably 24 hours a day excepting only when sleeping washing and bathing, for a period of time sufficient to resolve the trigger finger or thumb condition being treated. When used in this fashion, the positioning of the palm pad 14 over the inflamed tendon at the A1 pulley has a cushioning and protective effect on the tendon, allowing it to heal without being subject to further impact. The period of time necessary for resolving the condition varies from patient to patient and depends, in part, upon the severity of the condition and the diligence of the patient in wearing the digit pad 10 substantially 24 hours each day. Typically, a trigger finger or thumb condition treated in accordance with the present invention will resolve in a patient in about six to eight weeks.

Although the present invention has been described for use on a finger or thumb for the treatment of trigger finger or thumb, it is also possible to use the invention as a toe pad wherein the digit band fits onto a toe and the pad portion overlies a portion of the bottom of a foot. Of course, due to the difference in sizes between toes and fingers, different size bands and pads will be required for use on toes. The finger pad of the present invention also has many uses in sports activities to protect the palm of the hand during activities which involve grasping an object, such as golf, baseball, tennis, rowing, archery, and the like.

While the present invention has been described in terms of specific embodiments thereof, it will be understood that no limitations are intended to the details of construction or design or practice of the invention other than as defined in the appended claims.

The invention claimed is:

1. A digit pad for treating trigger finger and trigger thumb, comprising:
   a digit band adapted to be slid over the free end of the affected digit to a position wherein the proximal end of the band is at the MCP joint of the affected digit, said digit band being dimensioned and adapted to be positioned between the PIP and MCP joints of the affected digit, but not to overlie the PIP joint of the affected digit so as not to significantly interfere with the bending, use or functioning of the affected digit;
   a palm pad unitary with said digit band, said palm pad extending from the proximal end of the digit band toward the wrist, said palm pad being dimensioned and adapted to be positioned to overlie a portion of the palm to at least cover the A1 pulley of the affected digit, the proximal end of the palm pad extending beyond the A1 pulley, but not beyond the proximal palmer crease, said palm pad being at least as wide as the A1 pulley; and
   said digit pad being formed of a material which is soft, flexible, resilient and which has a sufficient density to protect the palm area which it overlies, and wherein neither the palm pad nor the digit band significantly interferes with the bending or use of the affected digit or hand.

2. A digit pad, as claimed in claim 1, wherein said digit band is endless.

3. A digit pad, as claimed in claim 1, wherein the proximal end of said palm pad extends to the neck of the metacarpal bone of the affected digit.

4. A digit pad, as claimed in claim 1, wherein said digit pad extends, in width, a sufficient distance on each side of the A1 pulley of the affected digit to substantially continuously overlie the A1 pulley as the affected hand is used.

5. A digit pad, as claimed in claim 1, wherein the width of said digit pad is from 1.5 to 2 times the width of the A1 pulley of the affected digit.

6. A digit pad, as claimed in claim 1, wherein said digit pad tapers from said digit band toward its proximal end, the width of said palm pad being greatest at the digit band.

7. A digit pad, as claimed in claim 1, wherein the proximal end of said digit pad defines a gentle curve.

8. A digit pad, as claimed in claim 1, wherein at least said palm pad is formed of neoprene sheet material laminated on opposing faces with nylon fabric.

9. A digit pad, as claimed in claim 1, wherein said digit band and said palm pad are formed of neoprene sheet material laminated on opposing faces with nylon fabric.

* * * * *